US010967525B2

(12) United States Patent
Kang

(10) Patent No.: US 10,967,525 B2
(45) Date of Patent: Apr. 6, 2021

(54) APPARATUS AND METHOD FOR PROVIDING AN ADJUSTABLE POSITIVE STOP IN SPACE

(71) Applicant: MAKO Surgical Corp., Fort Lauderdale, FL (US)

(72) Inventor: Hyosig Kang, Weston, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 0 days.

(21) Appl. No.: 16/530,455

(22) Filed: Aug. 2, 2019

(65) Prior Publication Data
US 2019/0351564 A1 Nov. 21, 2019

Related U.S. Application Data

(63) Continuation of application No. 15/218,926, filed on Jul. 25, 2016, now Pat. No. 10,369,708, which is a
(Continued)

(51) Int. Cl.
*A61B 34/30* (2016.01)
*B25J 9/10* (2006.01)
(Continued)

(52) U.S. Cl.
CPC ............ *B25J 17/0266* (2013.01); *A61B 34/10* (2016.02); *A61B 34/20* (2016.02); *A61B 34/30* (2016.02);
(Continued)

(58) Field of Classification Search
CPC ...... B25J 17/0266; B25J 9/0042; B25J 9/101; A61B 34/10; A61B 34/20; A61B 34/30; A61B 34/70; A61B 2034/102; A61B 2034/2055; A61B 2034/2065; A61B 2034/304; A61B 2090/034; A61B 90/39; A61B 2090/3945; A61B 2090/3983; A61B 90/03; G05B 2219/36432;
(Continued)

(56) References Cited

U.S. PATENT DOCUMENTS 4,216,467 A 8/1980 Colston
5,053,687 A * 10/1991 Merlet ............... F16H 21/46
318/568.2
(Continued)

OTHER PUBLICATIONS

European Office Action corresponding to EP Application No. 07 869 751.3, dated Nov. 24, 2009, 3 pages.
(Continued)

*Primary Examiner* — Stephen Holwerda
(74) *Attorney, Agent, or Firm* — Foley & Lardner LLP

(57) ABSTRACT

An apparatus for providing haptic guidance during manipulation of an end-effector includes a robotic arm. The robotic arm has at least one actuated joint, at least one other joint connected to the at least one actuated joint, and a physical constraint movable by actuation of the at least one actuated joint. The physical constraint limits the motion of the at least one other joint in at least one direction. The apparatus further includes an end-effector configured to be manipulated by an application of external forces and connected to the at least one other joint.

20 Claims, 6 Drawing Sheets

Related U.S. Application Data continuation of application No. 11/963,759, filed on Dec. 21, 2007, now Pat. No. 9,399,298.

(60) Provisional application No. 60/877,412, filed on Dec. 27, 2006.

(51) Int. Cl.

| | | |
|---|---|---|
| *B25J 17/02* | (2006.01) | |
| *A61B 34/20* | (2016.01) | |
| *A61B 34/00* | (2016.01) | |
| *B25J 9/00* | (2006.01) | |
| *A61B 34/10* | (2016.01) | |
| *A61B 90/00* | (2016.01) | |

(52) U.S. Cl.
CPC ............ *A61B 34/70* (2016.02); *B25J 9/0042* (2013.01); *B25J 9/101* (2013.01); *A61B 90/03* (2016.02); *A61B 90/39* (2016.02); *A61B 2034/102* (2016.02); *A61B 2034/2055* (2016.02); *A61B 2034/2065* (2016.02); *A61B 2034/304* (2016.02); *A61B 2090/034* (2016.02); *A61B 2090/3945* (2016.02); *A61B 2090/3983* (2016.02); *G05B 2219/36432* (2013.01); *G05B 2219/39432* (2013.01); *G05B 2219/45118* (2013.01); *G05B 2219/45123* (2013.01)

(58) Field of Classification Search
CPC ........... G05B 2219/39432; G05B 2219/45118; G05B 2219/45123
See application file for complete search history.

(56) References Cited

U.S. PATENT DOCUMENTS

| | | | | |
|---|---|---|---|---|
| 5,223,776 | A * | 6/1993 | Radke | B25J 13/02 |
| | | | | 200/5 R |
| 5,623,582 | A * | 4/1997 | Rosenberg | B25J 9/1689 |
| | | | | 700/264 |
| 5,651,574 | A * | 7/1997 | Tanikawa | B25J 7/00 |
| | | | | 294/86.4 |
| 5,656,905 | A | 8/1997 | Tsai | |
| 5,800,423 | A * | 9/1998 | Jensen | B25J 9/1065 |
| | | | | 606/1 |
| 5,807,377 | A * | 9/1998 | Madhani | A61B 34/77 |
| | | | | 606/1 |
| 6,493,608 | B1 | 12/2002 | Niemeyer | |
| 6,547,782 | B1 | 4/2003 | Taylor | |
| 2003/0053901 | A1* | 3/2003 | Roy | B25J 17/0266 |
| | | | | 414/735 |
| 2003/0176948 | A1* | 9/2003 | Green | H04N 13/239 |
| | | | | 700/264 |
| 2004/0024311 | A1* | 2/2004 | Quaid, III | A61B 34/10 |
| | | | | 600/428 |
| 2004/0091348 | A1 | 5/2004 | Kong et al. | |
| 2004/0146388 | A1 | 7/2004 | Khajepour et al. | |
| 2005/0156877 | A1 | 7/2005 | Schaeffer | |
| 2006/0142657 | A1 | 6/2006 | Quaid et al. | |
| 2007/0142657 | A1 | 6/2007 | Sarakinos et al. | |
| 2008/0010705 | A1 | 1/2008 | Quaid et al. | |

OTHER PUBLICATIONS

European Office Action corresponding to EP Application No. 07 869 751.3, dated Sep. 30, 2010, 6 pages.
International Preliminary Report on Patentability for PCT Application No. PCT/US2007/088568, dated Apr. 15, 2009, 15 pages.
International Search Report and Written Opinion for PCT Application No. PCT/US2007/088568, dated Jul. 1, 2008, 12 pages.

* cited by examiner

APPARATUS AND METHOD FOR PROVIDING AN ADJUSTABLE POSITIVE STOP IN SPACE

CROSS-REFERENCE TO RELATED PATENT APPLICATIONS

This application is a continuation of U.S. application Ser. No. 15/218,926, filed Jul. 25, 2016, which is a continuation of U.S. application Ser. No. 11/963,759, filed Dec. 21, 2007, which claims the benefit of and priority to U.S. Provisional Application No. 60/877,412, filed Dec. 27, 2006, both of which are hereby incorporated by reference herein in their entireties.

BACKGROUND

The disclosure relates generally to the field of robots and more specifically to the field of haptic robots.

Haptic interfaces permit a user to experience a sense of touch in a virtual or haptic environment. Such interfaces are finding acceptance in virtual reality games and in performing tasks that are virtually imaged. One area which uses haptic interfaces to help a user perform a task is computer aided surgery.

In computer aided surgery, a haptic interface can be used to provide haptic guidance to a surgeon. For example, a surgical instrument, such as a cutting tool, can be coupled to a haptic interface. The haptic interface may be, for example, part of a robotic device, such as a robotic arm. As the surgeon moves the surgical instrument in real space (e.g., to cut bone or other anatomy), constraints may be imposed on the surgeon through the haptic interface that limit his ability to manipulate the surgical instrument. For example, the surgeon's ability to manipulate the surgical instrument may be constrained so that the surgeon can only move the surgical instrument within a defined cutting region. The constraints may be based, for example, upon a desired relationship between the surgical instrument and the defined cutting region in real space. This real space relationship can be represented in a virtual environment as a relationship between a virtual instrument and a haptic object in virtual space, where the virtual instrument corresponds to the physical surgical instrument and the haptic object corresponds to the defined cutting region. In operation, the surgeon manipulates the surgical instrument while it is attached to the end of the haptic interface. Constraint feedback is provided to the surgeon through the haptic interface, which imposes a force on the surgeon sufficient to maintain the desired relationship between the virtual instrument and the haptic object.

For example, the haptic object may be a virtual protective boundary for an anatomic structure or a shape that is to be cut into bony anatomy. The virtual boundary is registered (or correlated) to the anatomy of a patient, and the virtual instrument is registered (or correlated) to the actual surgical instrument. To enable the surgeon to interact with the virtual environment via the haptic interface, a haptic rendering algorithm is employed. Haptic rendering is the process of computing and applying forces in response to user interactions with virtual objects. Using the haptic rendering algorithm, the haptic interface may be configured so that the force experienced by the surgeon increases as the virtual instrument approaches the virtual boundary. This increasing force provides a warning to the surgeon that he is near a forbidden region of the workspace (e.g., an anatomic structure of interest or other boundary) and therefore should proceed with caution in order to prevent unwanted penetration into and damage to the structure (for example, preventing a drill bit from entering too deeply into the bone). If the surgeon tries to force the instrument beyond the virtual boundary, the haptic interface provides an increasing force to prevent such motion. In this manner, the virtual boundary functions as a haptic stop to maintain the surgical instrument within a desired region of the workspace.

Preventing movement using a haptic stop, however, is typically accomplished with an admittance or impedance based system. An admittance device senses forces exerted by a user and responds by changing the position of the device (e.g., the position of the surgical instrument). Although admittance devices can provide stiff boundaries, they require force sensors and generally feel heavy to the user as the user moves the device through free space. In contrast, an impedance device senses a position of the device (e.g., a position of the surgical instrument) and responds by applying forces to the device by applying limited power to actuators of a backdrivable haptic interface system. Impedance devices generally feel relatively light to the user when moved through free space and are preferable for certain applications where the users wants to have a relatively light motion and to feel interaction forces with real objects when moving in free space. The output force of the actuators, however, is finite, and impedance devices are not able to generate boundaries as stiff as those generated by admittance devices. As a result, it may be possible for the surgeon to overcome the constraints imposed by the actuators and force the surgical instrument past the virtual boundary or haptic stop. This would result in unplanned damage to the tissue being operated upon.

What is needed is a haptic device having an adjustable positive stop that can provide haptic constraint forces sufficient to prevent erroneous movements by a user of the haptic device while still permitting the user to experience flexibility of motion during operation of the haptic device.

SUMMARY

One example embodiment of the invention relates to an apparatus comprising a mechanical positioner and first and second stops. The first and second stops are controllable by a drive mechanism to constrain movement of the mechanical positioner and thereby to constrain the ability of a user to manipulate an end-effector outside a predetermined range of motion. The first and second stops are further controllable by the drive mechanism to permit movement of the end-effector within the predetermined range of motion.

Another example embodiment relates to a method for constraining movement of an end-effector in space. The method comprises permitting a linkage joint to move freely when the end-effector is positioned a distance greater than a first predetermined value from a predetermined location in space. The method further comprises permitting the linkage joint to move freely within a predetermined range of motion defined by first and second stops when the end-effector is positioned a distance less than or equal to the first predetermined value and greater than a second predetermined value from the predetermined location in space. The method further comprises constraining the linkage joint from moving in a specific direction by one of the first and second stops when the end-effector is positioned a distance approximately equal to or less than the second predetermined value from the predetermined location in space. The constraining of the linkage joint constrains the movement of the end-effector in space.

BRIEF DESCRIPTION OF THE FIGURES

The invention is pointed out with particularity in the appended claims. The advantages of example embodiments of the invention described above, together with further advantages, may be better understood by referring to the following description taken in conjunction with the accompanying drawings. In the drawings, like reference characters generally refer to the same parts throughout the different views. The drawings are not necessarily to scale, emphasis instead generally being placed upon illustrating the principles of example embodiments of the invention.

DETAILED DESCRIPTION

Figure 1:
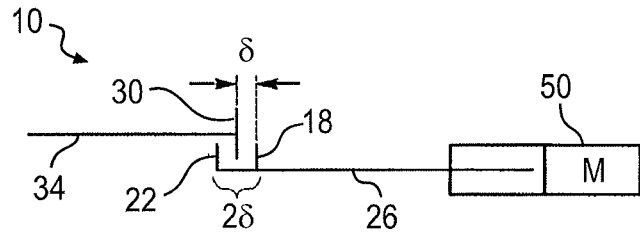
FIG. 1 is a schematic diagram of a positive stop haptic system of an embodiment of the invention.

In general, in various applications, when a tool or an instrument is being used, it is desirable to limit the range of possible movement of the tool. Limiting tool movement can prevent damage to a workpiece, for example, by preventing a user of the tool from cutting too deeply into the workpiece. When the user is operating a tool coupled to a robotic device in a particular process, such as surgery, manufacturing, or other applications, the limitations on tool movement can be implemented using physical stops.

In part, exemplary embodiments of the invention described herein include robotic devices that use different physical stops and controls suitable for constraining movement of a tool within a prescribed range of motion. This is accomplished by controlling the motion of different linkages and members of the robotic device such that for a particular range of motion or distance, parts of the device are allowed to travel freely while for other prescribed ranges of motion or distances, motion of the parts of the device is constrained in speed or halted altogether. Thus, the physical stops can be controlled to permit a user to move the tool in a desired region of a workspace and to constrain the ability of the user to manipulate the tool into a forbidden region of the workspace. Using actuators and tracking devices in combination with mechanical linkages and joints make such systems possible.

The exemplary embodiments also enable real time or dynamic positioning of a physical stop or constraint relative to a moving object. That is, for a moveable workpiece, such as a machineable block or a patient's hip bone, the example system described herein is able to respond to the motion of the workpiece by adjusting the physical stops in response thereto. This allows a surgeon or a worker to perform an operation on the patient or workpiece with the safety associated with the physical stops in spite of the movement of the patient or workpiece.

For example, in a medical application for a haptic device, the virtual environment created by a haptic rendering process includes virtual (or haptic) objects (such as guidewires, implant models, or protective boundaries) that interact with a virtual representation of a medical instrument. The virtual medical instrument is linked (or registered) to the physical medical instrument so that movement of the physical medical instrument results in corresponding movement of the virtual medical instrument. Similarly, the virtual object is linked (or registered) to the patient's physical anatomy so that movement of the physical anatomy results in corresponding movement of the haptic object. Because the virtual and physical environments are registered or associated with one another, the user's manipulation of the medical instrument is constrained based on interaction between the virtual object and the virtual representation of the medical instrument, which typically makes use of a point in virtual space termed the haptic interaction point (HIP). The HIP is a point in virtual space that corresponds to a physical point on the medical instrument, for example, the tip of a surgical burr or drill bit. As the HIP moves through virtual space, the haptic rendering algorithm computes forces based on a desired relationship between the HIP and the virtual object, such as a relationship where the boundaries of the virtual object define a permissible workspace (e.g., a desired region of the workspace or a predetermined range of motion in the workspace) and the HIP is maintained within the boundaries of the virtual object. The actuators of the haptic device generate the computed forces, and the haptic interface transmits these forces to the user in an effort to maintain the desired relationship. Thus, as the surgeon moves the physical instrument, he or she feels the forces that the HIP experiences in virtual space. In this way, movement of the medical instrument can be constrained, for example, to keep the medical instrument within a cutting boundary defined by the virtual object and to prevent the medical instrument from moving into a forbidden region of the workspace. Thus, the user is permitted to move the tool within the predetermined range of motion of the workspace, but the ability of the user to manipulate the tool outside the predetermined range of motion is constrained.

Thus, the movement of the HIP can be constrained to limit the way the surgeon can move the physical medical instrument. For example, the virtual object can be a virtual guidewire which constrains the HIP to move along a specific path. Attempted deviation from the path results in forces being generated that prevent or at least reduce the ability of the HIP to deviate from the path. These forces are transmitted to the surgeon through the haptic interface and thereby guide the physical instrument along a guide path in physical space in order to avoid anatomic features as the instrument is moved to a predefined location. In another example, the virtual object can be a virtual model of an implant to be implanted in a bone of a patient during a joint replacement operation. The virtual implant model is associated with (or registered to) the physical bone of the patient and defines the portion of bone to be removed so that a physical implant can be installed, as described, for example, in U.S. patent application Ser. No. 11/357,197, U.S. Pub. No. 2006/0142657, filed Feb. 21, 2006, and hereby incorporated by reference herein in its entirety. In the virtual environment, the HIP is constrained to stay within the cutting boundary defined by the implant model (i.e., the desired region of the workspace). If the HIP attempts to violate the boundary and to move into the forbidden region of the workspace, forces are transmitted to the surgeon through the haptic interface to prevent or at least reduce the surgeon's ability to violate the cutting boundary with the physical instrument.

Although the forces applied to the HIP in virtual space can become substantially infinite to prevent the HIP from progressing beyond a predefined point in virtual space, in a conventional haptic device, this "infinite" force is applied by the actuators and so in actuality will result in a less than infinite force being applied to the user through the haptic interface. As a result, the user, either intentionally or inadvertently, may overcome the constraint force to deviate from a guide path or violate a haptic boundary.

According to an embodiment of the present invention, a moveable positive stop is provided. One advantage of the moveable positive stop is that the positive stop can provide a sufficiently strong constraint to limit tool movement while still allowing the surgeon to retain flexibility of motion when moving the tool. FIG. 1 shown an embodiment of a positive stop haptic system 10 constructed in accordance with an exemplary embodiment of the invention. The positive stop haptic system 10 includes a drive mechanism 50, a mechanical positioner 30, an actuated linkage joint 26, a non-driven or passive linkage joint 34, a proximal positive stop 18, and a distal positive stop 22. The actuated linkage joint 26 and the passive linkage joint 34 form a prismatic joint assembly which permits relative linear motion between the actuated linkage joint 26 and the passive linkage joint 34.

The drive mechanism 50 is located at one end of the actuated linkage joint 26, and the positive stops 18 and 22 are located at the other end of the actuated linkage joint 26. As shown in FIG. 1, the distance between the positive stops 18 and 22 is indicated by (2D, and the midpoint distance between the positive stops 18 and 22 is δ. The mechanical positioner 30, which is disposed at one end of the passive linkage joint 34, is located between the proximal positive stop 18 and the distal positive stop 22. The other end of the passive linkage joint 34 is connected to an end-effector (not shown). The end-effector may be, for example, a medical instrument, a tool, or another link.

In operation, as the end-effector coupled to the passive linkage joint 34 is moved by a user (e.g., by a surgeon during a surgical procedure to sculpt bone), the mechanical positioner 30 moves between the proximal positive stop 18 and the distal positive stop 22. When the actuated linkage joint 26 is fixed in place by the drive mechanism 50, the positive stops 18 and 22 are also fixed in place and will prevent the mechanical positioner 30 from moving beyond the positive stops 18 and 22. In this manner, the positive stops 18 and 22 define a predetermined range of motion for the mechanical positioner 30 (and thus the end-effector) and function to permit movement of the end-effector within the predetermined range of motion and to constrain the user's ability to move the end-effector outside the predetermined range of motion. When desired, the drive mechanism 50 can be actuated to move the actuated linkage joint 26, which results in movement of the positive stops 18 and 22 toward or away from the drive mechanism 50. In this manner, the drive mechanism 50 is controllable to adjust the positive stops 18 and 22 to adjust the predetermined range of motion, such as to adjust the position in space of the predetermined range of motion. To enable free motion of the end-effector, the positive stops 18 and 22 can be configured to move when the mechanical positioner 30 moves so that the mechanical positioner 30 does not contact either the proximal positive stop 18 or the distal positive stop 22. This enables the user to move the end-effector freely because the mechanical positioner 30 has complete freedom of motion along the axis of the passive linkage joint 34. To enable the positive stops 18 and 22 to move with the mechanical positioner 30, the system can include a sensor to detect motion of the mechanical positioner 30 and a controller to control the drive mechanism 50 to move the actuated linkage joint 26 so that the positive stops 18 and 22 track along with the mechanical positioner 30 and thus do not contact the mechanical positioner 30. In this manner, the positive stops 18 and 22 can be adjusted in response to movement of the mechanical positioner 30. To trigger a physical stop (e.g., when the end-effector is near a forbidden region of the workspace), the drive mechanism 50 is halted, thereby preventing further motion of the positive stops 18 and 22. When the mechanical positioner 30 contacts one of the positive stops 18 and 22, the user's motion of the end-effector is constrained. In this manner, the positive stop haptic system 10 provides a moveable positive stop that can constrain the end-effector with a physical stop (as opposed to a stop based on forces generated by an actuator) that the user cannot overcome while still allowing the surgeon to retain flexibility of motion when moving.

Figure 2A:
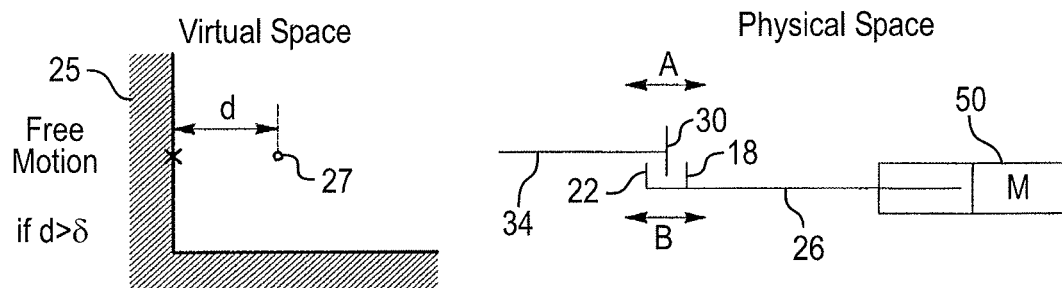
FIGS. 2a-2c are diagrams depicting the positive stop of FIG. 1 under a variety of conditions of a haptic interaction point moving in virtual space.
Figure 2B:
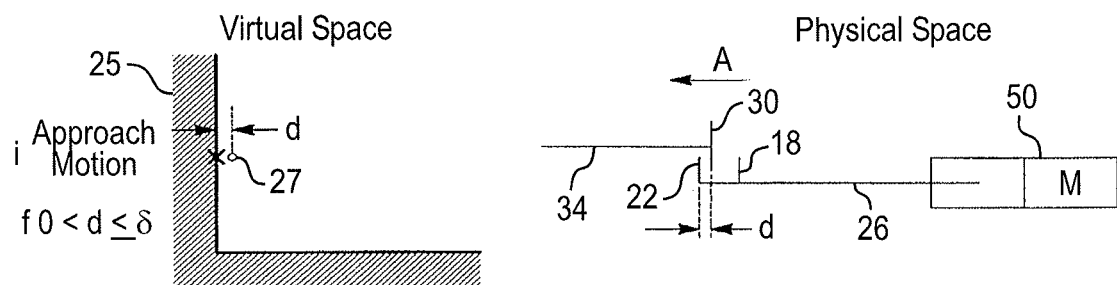
Figure 2C:
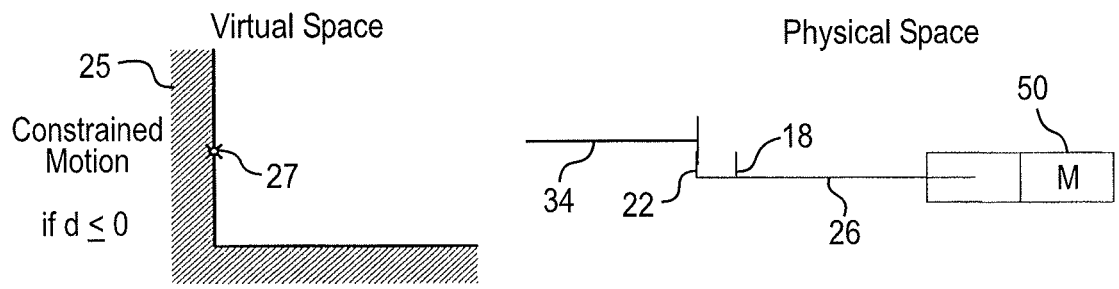

As discussed above, the position of a portion of the end-effector in physical space (such as the tip of the tool or instrument) corresponds to the HIP in virtual space. Thus, as the instrument or end-effector moves in real space, the HIP moves, for example, toward the virtual object in virtual space. Referring to FIGS. 2a-2c, when an HIP 27 is positioned a distance (d) from a portion of the virtual object 25, such as a boundary of the virtual object 25, one of three conditions are met. First, as shown in FIG. 2a, the value of (d) may be greater than a first predetermined value, for example, the distance between the mechanical positioner 30 and one of the positive stops 18 and 22 (d>(δ)). This condition is free motion. Second, as shown in FIG. 2b, the value of (d) may be greater than a second predetermined value and less than or equal to the first predetermined value (e.g., 0<d≤(δ)). This condition is approach motion. Third, as shown in FIG. 2c, (d) may be less than or equal to the second predetermined value (e.g., d≤0) meaning that the HIP 27 is at or within the virtual object boundary. This condition is constrained motion.

Referring to FIG. 2a, which illustrates free motion, when (d>(δ)), that is when the HIP 27 is located at a distance (d) that is greater than half the distance between the stops 18 and 22, the passive linkage joint 34 moves freely. The motion of the passive linkage joint 34 is free not only because the mechanical positioner 30 moves freely between the stops 18 and 22 (arrow A), but also because the actuated linkage joint 26 is driven by the drive mechanism 50 to track the motion of the mechanical positioner 30 so that the positive stops 18 and 22 also move (arrow B). The drive mechanism 50 preferably moves the actuated linkage joint 26 such that the distance between the mechanical positioner 30 and the proximal positive stop 18 or the distal positive stop 22 is nominally maintained at the midpoint distance δ.

Referring to FIG. 2b, which shows approach motion, once the HIP 27 is at a distance (d) equal to (δ), the drive mechanism 50 servos the actuated linkage joint 26 to resist further forward motion. This causes the distal positive stop 22 and the proximal positive stop 18 to become stationary and hence only allow the mechanical positioner 30 to move between the stops 18 and 22 (arrow A). Therefore, the passive linkage joint 34 can only move a maximum distance (δ) in a direction away from the actuated linkage joint 26 before the mechanical positioner 30 contacts the distal positive stop 22 preventing further motion. This then brings the HIP 27 to the surface of the object (d=0).

Referring to FIG. 2c, which shows constrained motion, once the HIP 27 has reached d=0, the mechanical positioner 30 contacts the distal positive stop 22, preventing further motion. Thus, the system provides a physical stop when the HIP 27 makes contact with the virtual object 25.

The example embodiments of the invention also relate to systems wherein the actuators and movable components are linked together in various suitable serial or parallel configurations. That is, in a series configuration, the drive mechanism 50 may be attached to the free end of the passive linkage joint of another positive stop assembly. Various medical applications, such as orthopedic surgery, are amenable to the techniques described herein.

Figure 3:
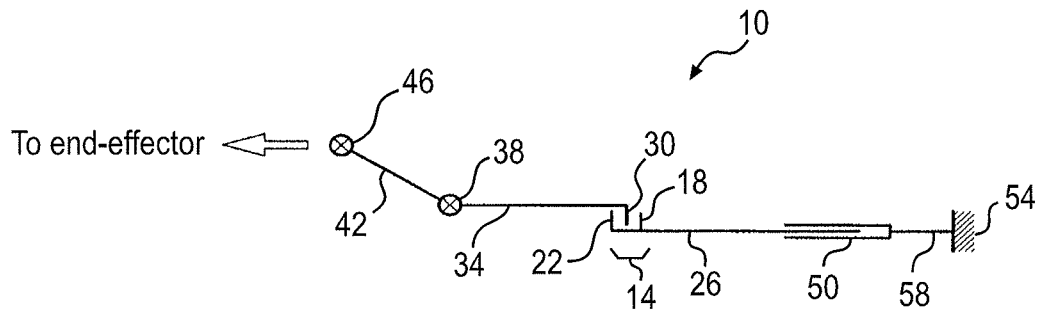
FIG. 3 is another schematic diagram of an embodiment of the invention of FIG. 1.

Referring to FIG. 3, a physical realization of a system 10 corresponding to an embodiment of a positive stop haptic system constructed in accordance with an exemplary embodiment of the invention includes a mechanical stop assembly 14, including a proximal positive stop 18 and a distal positive stop 22, attached to the distal end of an actuated linkage joint 26. The system 10 also includes a mechanical positioner 30 attached to the proximal end of a passive linkage joint 34. The passive linkage joint 34 can be moved freely (within the limits set by the positive stops 18 and 22) as long as the mechanical positioner 30 does not contact the proximal positive stop 18 or the distal positive stop 22.

As shown in FIG. 3, the distal end of the passive linkage joint 34 is attached to a revolute joint 38. The revolute joint 38 is also connected a distal link 42, which is connected to a second revolute joint 46. The second revolute joint 46 is connected to an end-effector (not shown).

In the embodiment of FIG. 3, the proximal end of the actuated linkage joint 26 is connected to the movable portion of a drive mechanism 50. The drive mechanism 50 includes a housing connected to a fixed base 54 by way of a proximal link 58. In various embodiments shown, the drive mechanism 50 can include, but is not limited to, an actuator or motor. For example, the actuator or motor can be linear, rotational, backdrivable, or non-backdrivable. A non-backdrivable mechanism 50 enhances the stiffness and margin of safety associated with the physical stop.

In operation, as the end-effector is moved by the user, the revolute joints 38 and 46 and the distal link 42 transmit the motion to the passive linkage joint 34, causing the mechanical positioner 30 to move between the proximal positive stop 18 and the distal positive stop 22. When either of the stops 18 or 22 is reached, the mechanical positioner 30 can move no further in the present direction. As a result, the end-effector is also prevented from moving further in that direction.

The position in space at which the positive stop occurs is determined in part by the position of the actuated linkage joint 26 within the drive mechanism 50. The drive mechanism 50 is fixed solidly to the base 54 by the proximal link 58. The drive mechanism 50 is used to position the actuated linkage joint 26 in space relative to the base 54.

Figure 3A:
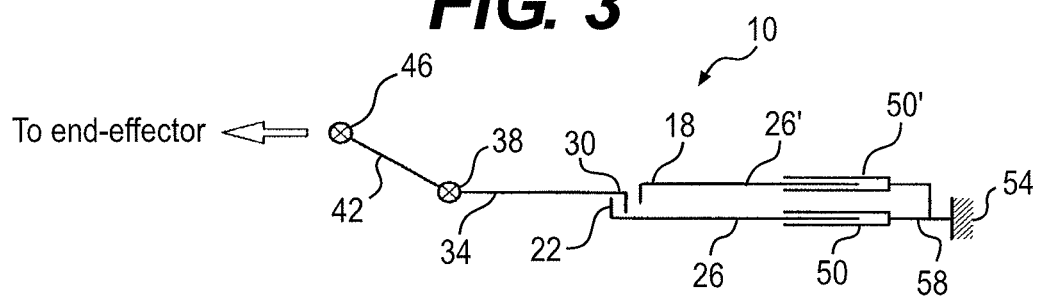
FIG. 3a is a schematic diagram of another embodiment of the invention having independent distal and proximal positive stops.

Referring to FIG. 3a, in another embodiment of the present invention, rather than have the distal positive stop 22 and the proximal positive stop 18 attached to a single actuated linkage joint 26 so that they are driven together, each positive stop 18 and 22 is attached to its own actuated linkage joint. As shown in FIG. 3a, the distal positive stop 22 is disposed on a first actuated linkage joint 26, and the proximal positive stop 18 is disposed on a second actuated linkage joint 26'. This embodiment utilizes a second drive mechanism 50' to drive the second actuated linkage joint 26'. In this embodiment, because each actuated linkage joint 26, 26' is driven by its own drive mechanism 50, 50', both of which are attached to the same base 54 or proximal link 58, the distance between the positive stops 18 and 22 is adjustable. Thus, not only can the location of the positive stop for the mechanical positioner 30 be determined (and adjusted), but the distance of travel (δ) for the mechanical positioner 30 between the positive stops 18 and 22 can also be adjusted. Thus, the drive mechanisms 50, 50' are controllable to adjust the positive stops 18, 22 to adjust the predetermined range of motion, such as to adjust the distance between the positive stops 18 and 22. This feature is beneficial when interacting with narrow constraint features that would otherwise require rapid motion of positive stops disposed on a common linkage joint (e.g., the actuated linkage joint 26 shown in FIG. 3) as the user alternately contacts the distal and proximal stops in quick succession.

Figure 3B:
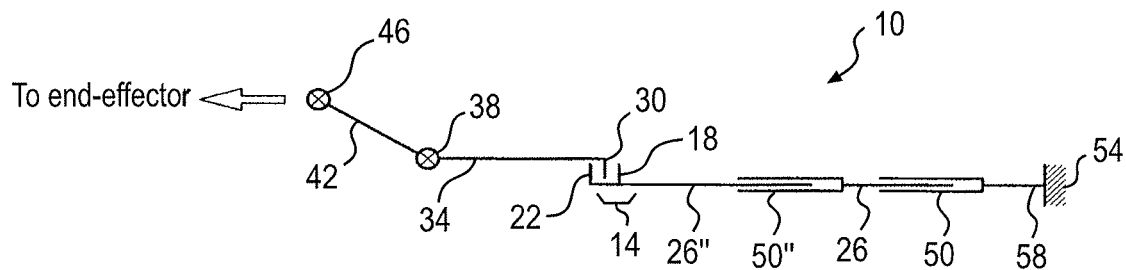
FIG. 3b is a schematic diagram of another embodiment of the invention having both micro and macro resolution drive mechanisms.

Referring to FIG. 3b, in yet another embodiment, a second drive mechanism 50" is connected to the actuated linkage joint 26 of the first drive mechanism 50. In this embodiment, a second actuated linkage joint 26" is driven by the second drive mechanism 50". The second actuated linkage joint 26" includes the mechanical stop assembly 14. In this embodiment, the drive mechanism 50 and the drive mechanism 50" have different resolutions and/or different ranges of motion. Thus, for example, the drive mechanism 50 may have a coarser granularity and larger range of motion than the drive mechanism 50". This embodiment permits the coarser macro drive mechanism 50 to locate the general location of the positive stops 18 and 22 by determining the general location of the actuated linkage joint 26, and permits the finer micro drive mechanism 50" to set the ultimate fine position of the positive stops 18 and 22. This embodiment can also be used in conjunction with the embodiment shown in FIG. 3a to provide for adjustable positive stops with coarse and fine positioning.

Figure 3C:
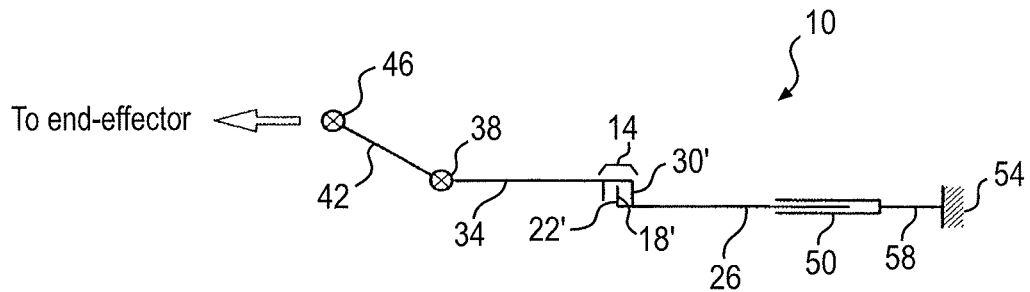
FIG. 3c is a schematic diagram of another embodiment of the invention illustrating a mechanical positioner and positive stops having different shapes.

Referring to FIG. 3c, in other embodiments, as will be recognized by one of skill in the art, the form of the mechanical positioner 30 and the positive stops 18, 22 may be altered in any manner appropriate for accomplishing the objective of constraining the user's ability to move the end effector. For example, in contrast to FIGS. 1-3b, which illustrate positive stops 18 and 22 that form a "concave" or "female" shape and a mechanical positioner 30 having a "convex" or "male" shape, the positive stop device may include a mechanical positioner 30' having a concave shape and positive stops 18' and 22' having a convex shape as shown in FIG. 3c. The geometry of the mechanical positioner 30' and the positive stops 18' and 22' can be adjusted as desired to achieve the desired constraint.

Figure 4:
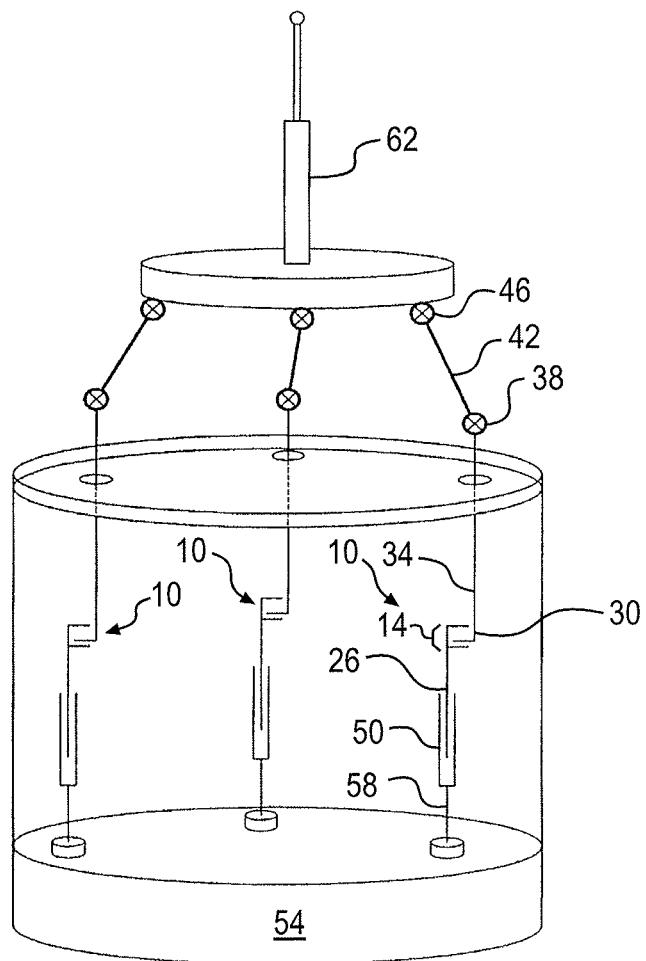
FIG. 4 is a schematic diagram of an embodiment of a plurality of the positive stop haptic systems of FIG. 1 arranged to constrain an end-effector.
Figure 5:
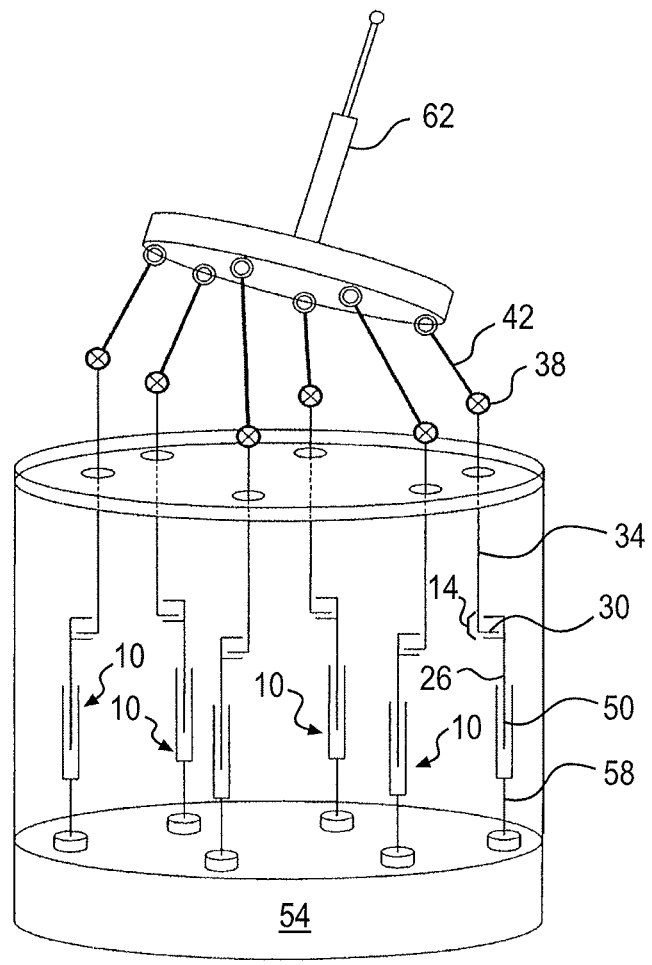
FIG. 5 is a schematic diagram of another embodiment of a plurality of the positive stop haptic systems of FIG. 1 arranged to constrain an end-effector.

Referring to FIG. 4, three positive stop haptic systems 10 are shown positioned between an end-effector 62 and a base 54. The positioning of multiple positive stop haptic systems 10 permits constraints to be applied over multiple degrees of freedom. As shown in FIG. 5, by placing multiple positive stop haptic systems 10, generally six in total, in conjunction with the end-effector 62, the end-effector 62 can be constrained to stop at an arbitrary point in physical space.

Figure 6:
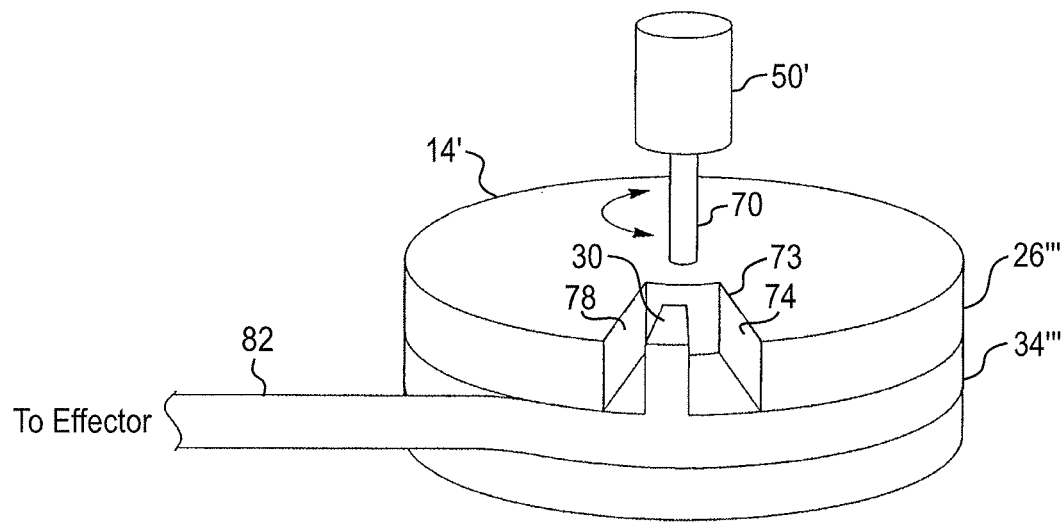
FIG. 6 is a schematic diagram of a positive stop haptic system of an embodiment of the invention utilizing rotary motion.

Referring to FIG. 6, an exemplary embodiment of the invention can also be used to constrain the end-effector using rotary motion. In FIG. 6, a revolute joint assembly is shown which permits a relative rotational motion between an actuated linkage joint 26''' and a passive linkage joint 34'''. To constrain the end-effector using rotary motion, a rotary mechanical stop assembly 14' is attached along its axis of rotation to a rotational motor 50' by a drive shaft 70. In the embodiment shown, the common mount to ground or the base of another apparatus is not depicted. The rotating elements share a common axis and typically a common mount. In one embodiment, the mechanical stop assembly 14' incorporates a notch 73 in the circumference of the mechanical stop assembly 14' to define a first positive stop 74 and a second positive stop 78. The mechanical stop assembly 14' is mounted on, and coaxially with, the passive linkage joint 34'. The passive linkage joint 34''' includes a mechanical positioner 30 that extends into the notch 73. The motor 50' causes the mechanical stop assembly 14' to rotate, thereby positioning the notch 73 at a predetermined angle so that the first positive stop 74 and the second positive stop 78 can be made to constrain movement of the mechanical positioner 30.

The passive linkage joint 34''' is connected to an upper link (e.g., an end-effector or other link) by a distal link 82. As the upper link is moved, the distal link 82 causes the passive linkage joint 34' to rotate until the mechanical positioner 30 contacts either the first positive stop 74 or second positive stop 78. By causing the motor 50' to rotate from a first position to a second position, the positions at which the mechanical positioner 30 contacts the positive stops 74 and 78 is changed thereby changing the constraint placed on the end-effector. Thus, in the embodiment of FIG. 6, the positive stop is adjustable to enable real time or dynamic positioning of the positive stop relative to a movable workpiece. Additionally, the previously described embodiments of FIGS. 1-3c can compensate for workpiece movement in a similar manner. For example, by adjusting the position of the positive stops 18 and 22, the location of the predetermined range of motion can be changed to correspond to a changed position of the workpiece.

Figure 7:
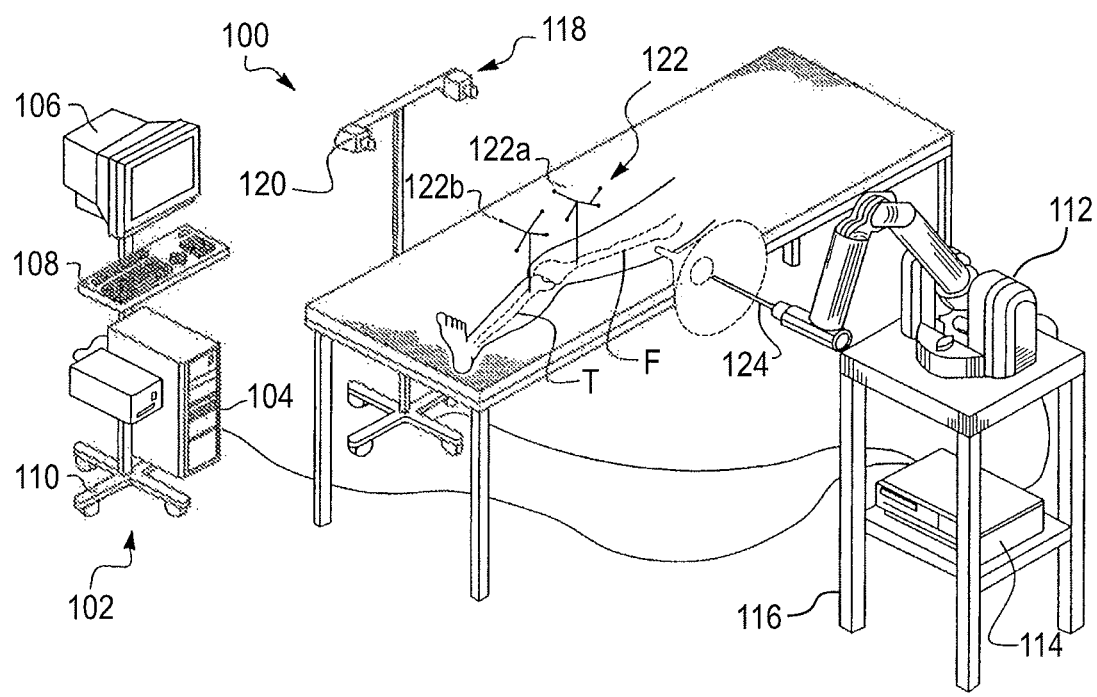
FIG. 7 is a schematic diagram of a surgical system of an embodiment of the invention.

One application of the present invention involving a moveable workpiece is a surgical application involving cutting or sculpting of bone, such as orthopedic joint replacement. Referring to FIG. 7, a surgical system 100 for a knee replacement procedure is shown. To detect motion of the workpiece (i.e., a femur F and/or a tibia T), the surgical system 100 includes a tracking system 118 configured to track one or more objects during the surgical procedure to detect movement of the objects. The tracking system 118 includes a detection device 120 that obtains a pose (i.e., position and orientation) of an object with respect to a coordinate frame of reference of the detection device 120. As the object moves in the coordinate frame of reference, the detection device 120 tracks the object. A change in the pose of the object indicates that the object has moved. In response, a computing system 102 can make appropriate adjustments to control parameters for a haptic device 112 (e.g., a robotic arm) mounted on a platform 116. For example, when the anatomy (e.g., the femur F or the tibia T) moves, the computing system 102 can make a corresponding adjustment to a virtual haptic object (e.g., a virtual cutting boundary) that is registered to the anatomy. Thus, the virtual cutting boundary moves along with the anatomy. As the virtual cutting boundary moves, the position of the positive stops of embodiments of the present invention can be adjusted accordingly, for example, as described above. The computing system 102 includes hardware and software for operation and control of the surgical system 100 and may comprise a computer 104, a computer 114, a display device 106, an input device 108, and a cart 110. Computer 114 includes haptic control utilities and programs that enable the haptic device 112 to utilize data from the tracking system 118.

The tracking system 118 may be any tracking system that enables the surgical system 100 to continually determine (or track) a pose of the relevant anatomy of the patient and a pose of a tool 124 (and/or the haptic device 112). For example, the tracking system 118 may comprise a non-mechanical tracking system, a mechanical tracking system, or any combination of non-mechanical and mechanical tracking systems suitable for use in a surgical environment.

In one embodiment, the tracking system 118 includes a non-mechanical tracking system as shown in FIG. 7. The non-mechanical tracking system is an optical tracking system that comprises a detection device 120 and a trackable element (or tracker) that is configured to be disposed on a tracked object (such as the relevant anatomy) and is detectable by the detection device 120. In one embodiment, the detection device 120 includes a visible light-based detector, such as a micron tracker, that detects a pattern (e.g., a checkerboard pattern) on a tracking element. In another embodiment, the detection device 120 includes a stereo camera pair sensitive to infrared radiation and positionable in an operating room where the surgical procedure will be performed. The tracker is configured to be affixed to the tracked object in a secure and stable manner and includes an array of markers (e.g., an array S1 shown in FIG. 8) having a known geometric relationship to the tracked object. As is well known, the markers may be active (e.g., light emitting diodes or LEDs) or passive (e.g., reflective spheres, a checkerboard pattern, etc.) and have a unique geometry (e.g., a unique geometric arrangement of the markers) or, in the case of active, wired markers, a unique firing pattern. In operation, the detection device 120 detects positions of the markers, and the surgical system 100 (e.g., the detection device 120 using embedded electronics) calculates a pose of the tracked object based on the markers' positions, unique geometry, and known geometric relationship to the tracked object. The tracking system 118 includes a tracker for each object the user desires to track, such as an anatomy tracker 122 (to track patient anatomy), a haptic device tracker (to track a global or gross position of the haptic device 112), an end effector tracker (to track a distal end of the haptic device 112), and an instrument tracker (to track an instrument held manually by the user).

Figure 8:
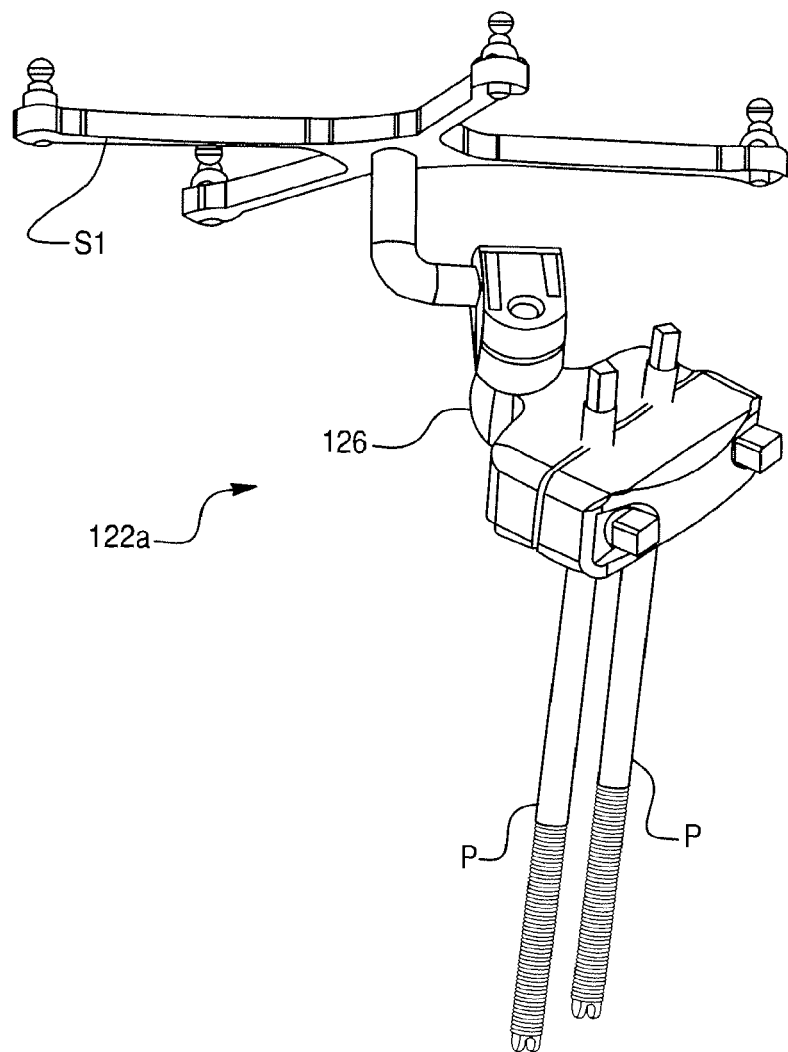
FIG. 8 is a perspective view of an anatomy tracker.

In one embodiment, an anatomy tracker 122 is disposed on the patient's anatomy and enables the anatomy to be tracked by the detection device 120. The anatomy tracker 122 includes a fixation device for attachment to the anatomy, such as a bone pin, surgical staple, screw, clamp, intramedullary rod, or the like. In one embodiment, the anatomy tracker 122 is configured for use during knee replacement surgery to track a femur F and a tibia T of a patient. In this embodiment, as shown in FIG. 7, the anatomy tracker 122 includes a first tracker 122a adapted to be disposed on the femur F and a second tracker 122b adapted to be disposed on the tibia T. As shown in FIG. 8, the first tracker 122a includes a fixation device comprising bone pins P, a clamp 126, and a unique array S1 of markers (e.g., reflective spheres). The second tracker 122b is identical to the first tracker 122a except the second tracker 122b is installed on the tibia T and has its own unique array of markers. When installed on the patient, the first and second trackers 122a and 122b enable the detection device 120 to track a position of the femur F and the tibia T. U.S. patent application Ser. No. 11/750,840, filed May 18, 2007, entitled "Method and Apparatus for Controlling a Haptic Device," hereby incorporated by reference herein in its entirety, provides additional details regarding the arrangement shown in FIGS. 7 and 8. Additionally, paragraphs [0063]-[0081] of the above-referenced U.S. patent application Ser. No. 11/750,840 provide details regarding a technique for compensating for motion of objects (patient, surgical tool, robot) during a surgical procedure without interrupting operation of the surgical device during the surgical procedure.

Although embodiments of this invention have been described in terms of a haptic medical application, as stated previously, this invention can be used to provide movable positive stops for other applications.

While the present invention has been described in terms of certain example embodiments, it will be readily understood and appreciated by one of ordinary skill in the art that it is not so limited, and that many additions, deletions, and modifications to the example embodiments may be made within the scope of the invention as hereinafter claimed. Accordingly, the scope of the invention is limited only by the scope of the appended claims.

What is claimed is:

1. An apparatus, comprising:
at least one actuated joint,
at least one passive joint connected to the at least one actuated joint,
a physical constraint movable by actuation of the at least one actuated joint, and
a cutting tool connected to the at least one passive joint and moveable relative to the physical constraint by physical manipulation of the cutting tool by a user;
wherein the physical constraint is configured to provide haptic feedback to the user during the physical manipulation of the cutting tool by limiting a range of motion of the passive joint in at least one direction.

2. The apparatus of claim 1, wherein the at least one passive joint provides for movement under physical manipulation by a user and the at least one actuated joint provides for movement under actuation by an electrical motor.

3. The apparatus of claim 1, wherein the cutting tool is a surgical burr.

4. The apparatus of claim 1, wherein the cutting tool is a drill bit.

5. The apparatus of claim 1, wherein the physical constraint permits movement of the cutting tool within a predetermined range of motion and constrains movement of the cutting tool outside the predetermined range of motion.

6. The apparatus of claim 1, wherein the at least one actuated joint includes an active linkage controlled by a drive mechanism, wherein the drive mechanism is configured to control a location of the physical constraint based on a position of a virtual object in a virtual space.

7. The apparatus of claim 6, wherein the drive mechanism is configured to adjust the location of the physical constraint in response to a current position of the cutting tool.

8. The apparatus of claim 7, wherein the current position of the cutting tool is determined using a tracking system.

9. The apparatus of claim 1, wherein the physical constraint comprises a pair of stops.

10. A method for controlling a user's movements of an end-effector, comprising:
receiving a user-applied force on the end-effector of a robotic arm causing motion at joints of the robotic arm;
determining a current position of the end-effector relative to an anatomy of a patient;
comparing a current position of the end-effector to a predetermined location defined relative to the anatomy; and
controlling a position of a physical constraint based on the comparison between the current position of the end-effector and the predetermined location, wherein the physical constraint is configured to constrain movement of the end-effector resulting from the user-applied force by limiting a range of motion of a passive joint coupled between the end effector and the physical constraint.

11. The method of claim 10, wherein the current position of the end-effector is determined using a tracking system.

12. The method of claim 10, wherein the predetermined location in space is based on a position of a virtual object in a virtual space.

13. A system for providing feedback, comprising:
a passive joint movable about an axis;
an end-effector coupled to the passive joint and configured to be manipulated by an application of external forces on the end-effector; and
a physical constraint selectively driven about the axis to limit a range of motion of the passive joint in at least one direction to constrain movement of the end-effector as the end-effector is moved relative to the physical constraint by user manipulation of the end-effector.

14. The system of claim 13, wherein the passive joint is rotatable about the axis and the physical constraint is rotatable about the axis, the physical constraint including a portion that lies within a plane that includes the passive joint so as to limit movement of the end-effector when the passive joint and physical constraint are in contact with one another.

15. The system of claim 13, wherein the end-effector is a bone cutting tool.

16. The system of claim 13, wherein the at least one direction comprises rotation about the axis.

17. The system of claim 13, wherein the physical constraint has a sensor associated therewith that measures a position of the physical constraint, the system further including:
a controller including:
in communication with the second sensor and a motor that drives the physical constraint; and
a computer in communication with the controller and configured to track the location of the physical constraint via information received from the second sensor.

18. The system of claim 17, wherein the controller is configured to execute a control program that determines a position in which the physical constraint must be placed based on a surgical plan.

19. The system of claim 13, wherein a position of the physical constraint is dynamically controlled in order to create a physical barrier to motion of the end-effector in accordance with a surgical plan.

20. The system of claim 13, wherein the feedback is haptic feedback.

* * * * *